(12) United States Patent
Langlois et al.

(10) Patent No.: US 6,835,843 B2
(45) Date of Patent: Dec. 28, 2004

(54) METHOD FOR SYNTHESIS OF PERINDOPRIL AND ITS PHARMACEUTICALLY ACCEPTABLE SALTS

(75) Inventors: Pascal Langlois, Saint Eustache la Foret (FR); Hugues Turbe, Villers-Ecalle (FR)

(73) Assignee: Les Laboratoires Servier, Courbevoie (FR)

( * ) Notice: Subject to any disclaimer, the term of this patent is extended or adjusted under 35 U.S.C. 154(b) by 0 days.

(21) Appl. No.: 10/239,129

(22) PCT Filed: Apr. 5, 2001

(86) PCT No.: PCT/FR01/01026
§ 371 (c)(1),
(2), (4) Date: Sep. 19, 2002

(87) PCT Pub. No.: WO01/58868
PCT Pub. Date: Aug. 16, 2001

(65) Prior Publication Data
US 2003/0069431 A1 Apr. 10, 2003

(30) Foreign Application Priority Data
Apr. 6, 2000 (FR) .......................................... 00 04379

(51) Int. Cl.⁷ ............................................. C07D 209/42
(52) U.S. Cl. ....................................................... 548/452
(58) Field of Search .......................................... 548/452

(56) References Cited
U.S. PATENT DOCUMENTS
4,914,214 A * 4/1990 Vincent et al. ............. 548/492

FOREIGN PATENT DOCUMENTS

| EP | 0049658 | 4/1982 |
|---|---|---|
| EP | 0116842 | 8/1984 |
| EP | 0308341 | 3/1989 |
| EP | 0309324 | 3/1989 |

OTHER PUBLICATIONS

Vincent, et al., *Drug Design and Discovery*, vol. 9, No. 1, 1992, pp. 11–28.

* cited by examiner

Primary Examiner—Joseph K. McKane
Assistant Examiner—Rebecca Anderson
(74) Attorney, Agent, or Firm—The Firm of Hueschen and Sage

(57) ABSTRACT

The invention concerns a method for synthesis of perindopril of formula (I) and its pharmaceutically acceptable salts

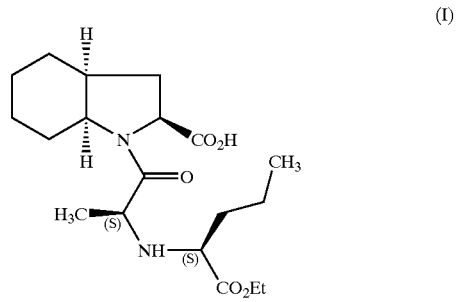

4 Claims, No Drawings

METHOD FOR SYNTHESIS OF PERINDOPRIL AND ITS PHARMACEUTICALLY ACCEPTABLE SALTS

This application is a 371 of PCT/FR01/01026 which was filed Apr. 5, 2001.

The present invention relates to a process for the industrial synthesis of perindopril of formula (I):

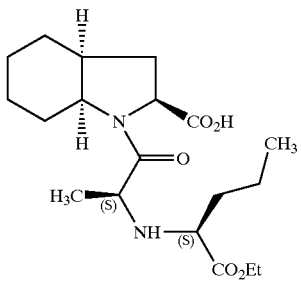

and pharmaceutically acceptable salts thereof.

Perindopril, and also pharmaceutically acceptable salts thereof, and more especially the tert-butylamine salt thereof, have valuable pharmacological properties. Their principal property lies in the inhibition of the enzyme that converts angiotensin I (or kininase II), which enables on the one hand prevention of the conversion of the decapeptide angiotensin I to the octapeptide angiotensin II (vasoconstrictor) and on the other hand prevention of the degradation of bradykinin (vasodilator) to inactive peptide. Those two actions contribute to the beneficial effects of perindopril in cardiovascular disorders, especially arterial hypertension and cardiac insufficiency.

Perindopril, its preparation and its therapeutic use have been described in European Patent Specification EP 0 049 658.

Given the pharmaceutical interest in that compound, it is important to be able to obtain it by an effective industrial synthesising process that can readily be applied on an industrial scale, yielding perindopril in a good yield and, especially, with an excellent degree of purity.

The Patent Specification EP 0 308 341 describes the industrial synthesis of perindopril by the coupling of (2S, 3aS,7aS)-octahydroindole-2-carboxylic acid benzyl ester with N-[(S)-1-carboxybutyl]-(S)-alanine ethyl ester, followed by deprotection of the carboxylic group of the heterocycle by catalytic hydrogenation. That process has the advantage of yielding perindopril in a good yield from starting materials for which industrial synthesis has already been described. However, the purity of the perindopril obtained by that process is not satisfactory, and necessitates a purification step in order to obtain perindopril of a quality that would allow its use as a pharmaceutical active ingredient. Indeed, under the conditions described in that patent specification the perindopril obtained is contaminated by significant amounts of the impurities of formulae (II) and (III)

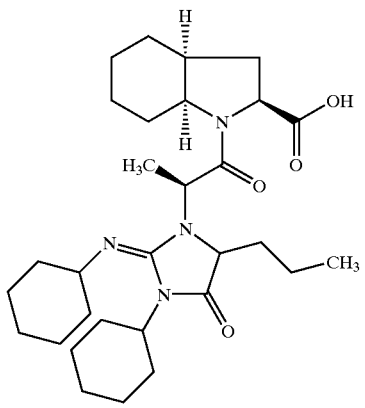

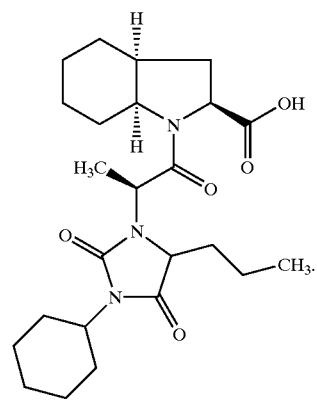

The Applicant has now developed a new industrial synthesising process that yields perindopril in a degree of purity that is compatible with its use as a pharmaceutical active ingredient, the levels of impurities of formulae (II) and (III) being less than 0.2% and 0.1%, respectively.

More specifically, the present invention relates to a process for the industrial synthesis of perindopril which is characterised in that the benzyl ester of formula (IV):

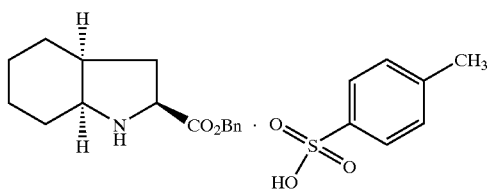

wherein Bn represents the benzyl group, is reacted with the compound of formula (V):

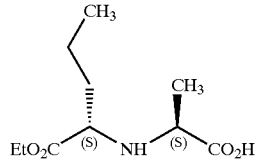

in ethyl acetate, in the presence of an amount of from 0.4 to 0.6 mol of 1-hydroxybenzotriazole per mol of compound of formula (IV) employed and in the presence of an amount of from 1 to 1.2 mol of dicyclohexylcarbodiimide per mol of compound of formula (IV) employed, in the absence of triethylamine or in the presence of an amount of triethylamine that is less than or equal to 1 mol per mol of compound of formula (IV) employed, preferably less than or equal to 0.25 mol per mol of compound of formula (IV) employed, at a temperature of from 20 to 77° C., to yield, after isolation, the compound of formula (VI):

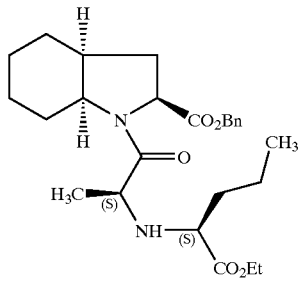

(VI)

wherein Bn represents the benzyl group, the carboxylic group of the heterocycle of which is deprotected by catalytic hydrogenation to yield perindopril of formula (I), which is converted, if desired, into a pharmaceutically acceptable salt, such as the tert-butylamine salt.

The process is of particular interest for the following reasons:

The coupling in alkaline medium of the benzyl ester of formula (IV) with the compound of formula (V) has been described in the Patent Specification EP 0 308 341. But, under the conditions described (the use of 3 mols of compound of formula (V), 3 mol of triethylamine, 3.8 mol of 1-hydroxybenzotriazole and 2.9 mol of dicyclohexylcarbodiimide per mol of compound of formula (IV) employed), numerous secondary products are formed. In particular, the compound of formula (VI) obtained contains in significant amounts (5 to 15%) the impurities of formulae (VII) and (VIII) which, when debenzylation is carried out, result in the impurities of formulae (II) and (III)

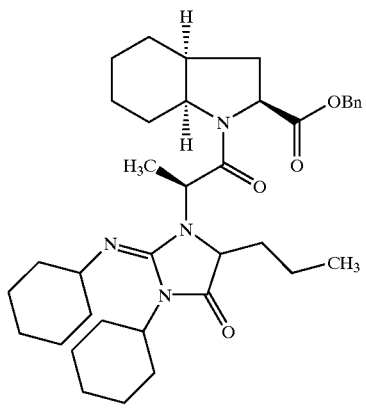

(VII)

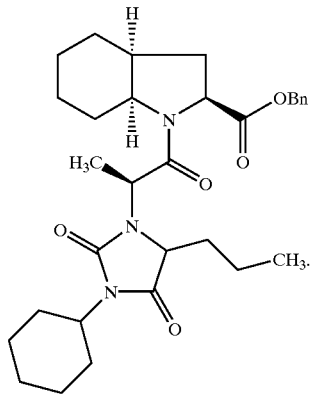

(VIII)

The Applicant has found, unexpectedly, that the reduction, or even omission, of triethylamine in the coupling step, has made it possible to restrict the levels of impurities of formulae (VII) and (VIII) in the compound of formula (VI) to less than 1.5%.

The catalytic hydrogenation of the compound of formula (VI) so obtained yields perindopril of far better purity, and in particular with levels of impurities of formulae (II) and (III) of less than 0.2% and 0.1%, respectively.

In addition, the reduction, in the coupling step, of the amount of compound of formula (V), of 1-hydroxybenzotriazole and of dicyclohexylcarbodiimide, enables a yield of compound of formula (VI) to be obtained that is as good as that obtained with larger amounts of reagents, thus making the process far more advantageous on an industrial scale.

The Examples below illustrate the invention but do not limit it in any way.

EXAMPLE 1

Benzyl (2S,3aS, 7aS)-1-{(2S)-2-[(1S)-1-(ethoxycarbonyl)-butylamino]-propionyl}-octahydro-1H-indole-2-carboxylate There are introduced into a reactor, with stirring, 1 kg of (2S,3aS,7aS)-octahydroindole-2-carboxylic acid benzyl ester para-toluenesulfonate, 0.06 kg of triethylamine, 4.6 liters of ethyl acetate and then, after stirring for 10 minutes at ambient temperature, 0.52 kg of N-[(S)-ethoxycarbonyl-1-butyl]-(S)-alanine, 0.15 kg of 1-hydroxybenzotriazole and 0.5 kg of dicylohexylcarbodiimide. The heterogeneous mixture is then brought to 30° C. for 3 hours while stirring well, and is subsequently cooled to 0° C. and filtered. The filtrate is then washed and subsequently evaporated to dryess to produce the expected product in a yield of 92%.

EXAMPLE 2

(2S,3aS,7aS)-1-{(2S)-2-[(1S)-1-(Ethoxycarbonyl)-butylamino]-propionyl}-octahydro-1H-indole-2-carboxylic acid The residue obtained in the preceding step (1 kg) is dissolved in 1 liter of methylcyclohexane and the solution is transferred to a hydrogenator; 0.13 kg of 5% palladium-on-carbon suspended in 0.4 liters of methylcyclohexane are then added, followed by 3.2 liters of water. The mixture is then hydrogenated under a pressure of 0.5 bar at a temperature of from 15 to 30° C. until the theoretical amount of hydrogen has been absorbed. After removal of the catalyst by filtration, the aqueous phase of the filtrate is washed with methylcyclohexane and then lyophilised to produce the expected product in a yield of 94%.

EXAMPLE 3

(2S,3aS,7aS)-1-{(2S)-2-[(1S)-1-(ethoxycarbonyl)-butylamino]-propionyl}-octahydro-1H-indole-2-carboxylic acid tert-butylamine salt The lyophilisate obtained in the preceding step (1 kg) is dissolved in 14 liters of ethyl acetate; 0.2 kg of tert-butylamine and 2 liters of ethyl acetate are then added. The suspension obtained is subsequently heated at reflux until complete dissolution is achieved, and the resulting solution is then filtered while hot and cooled, with stirring, to a temperature of 15–20° C. The precipitate obtained is then filtered off, made into a paste again with ethyl acetate, dried and then ground to produce the expected product in a yield of 95%.

We claim:

1. A process for the industrial synthesis of perindopril of formula (I)

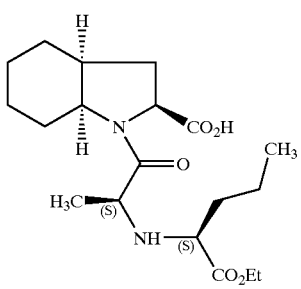

(I)

or a pharmaceutically acceptable salts thereof, wherein the benzyl ester of formula (IV):

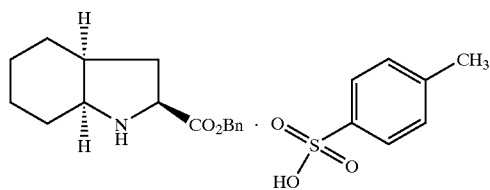

(IV)

in which Bn represents benzyl, is reacted with the compound of formula (V):

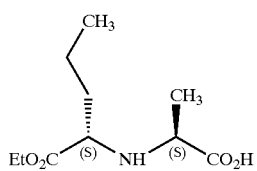

(V)

in ethyl acetate, in the presence of an amount of from 0.4 to 0.6 mol of 1-hydroxybenzotriazole per mol of the compound of formula (IV) employed and in the presence of an amount of from 1 to 1.2 mol of dicyclohexylcarbodiimide per mol of compound of formula (IV) employed, in the absence of triethylamine, at a temperature of 20 to 77° C., to yield, after isolation, the compound of formula (VI):

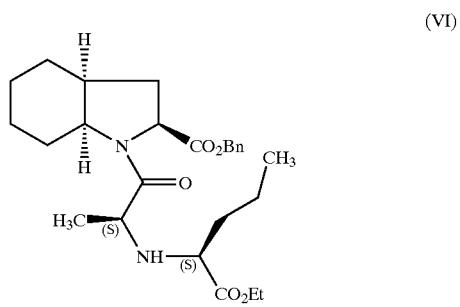

(VI)

which is low in the impurities of formulae (VII) and (VIII)

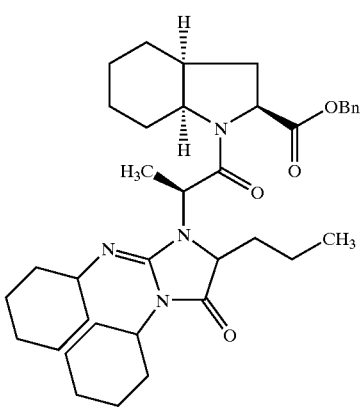

(VII)

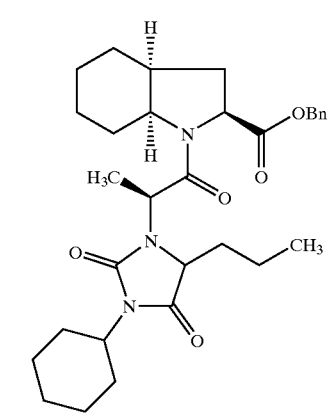

(VIII)

in which Bn represents benzyl, and the carboxylic group of the heterocycle of the formula (IV) is deprotected by catalytic hydrogenation to yield perindopril of formula (I), which is low in the impurities of formulae (II) and (III):

(II)

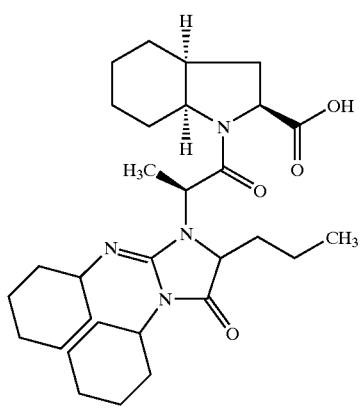

(III)

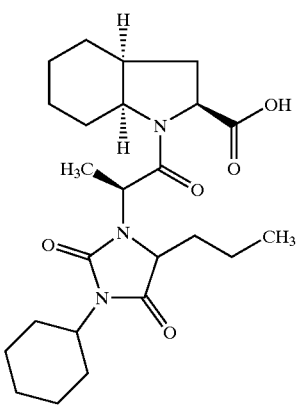

wherein the perindopril is converted, if desired, into a pharmaceutically acceptable salt.

2. The process of claim 1 for the synthesis of perindopril in the form of its tert-butylamine salt.

3. The process of claim 1, wherein the compound of formula (VI) is obtained with a level of impurities of formulae (VII) and (VIII) that is less than 1.5%

(VII)

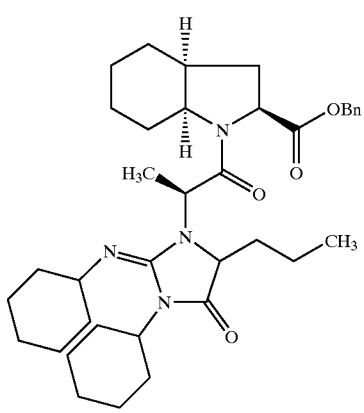

(VIII)

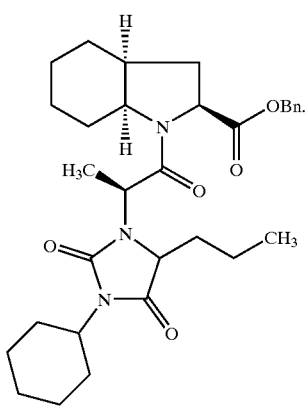

4. The process of claim 1, wherein the perindopril is obtained with levels of impurities of formulae (II) and (III) that are less than 0.2% and 0.1%, respectively (II)

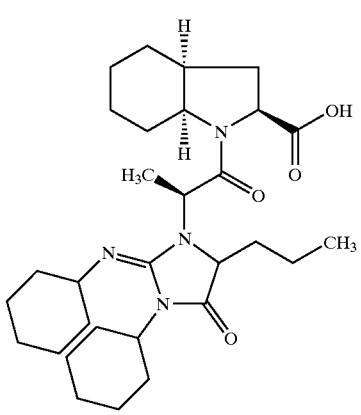

(III)

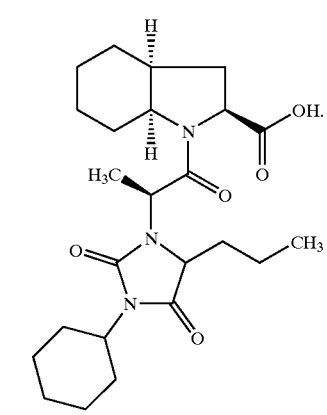

* * * * *